United States Patent
Ramsauer

(10) Patent No.: US 7,315,607 B2
(45) Date of Patent: Jan. 1, 2008

(54) MAMMOGRAPH SYSTEM WITH A FACE SHIELD

(75) Inventor: Martin Ramsauer, Pyrbaum (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 11/511,615

(22) Filed: Aug. 29, 2006

(65) Prior Publication Data
US 2007/0058774 A1 Mar. 15, 2007

(30) Foreign Application Priority Data
Sep. 2, 2005 (DE) .................. 20 2005 013 910 U

(51) Int. Cl.
*A61B 6/04* (2006.01)
(52) U.S. Cl. ........................ 378/37; 378/203
(58) Field of Classification Search ................ 378/119, 378/161, 142, 160, 203, 37, 55, 145, 196, 378/197, 204
See application file for complete search history.

(56) References Cited

U.S. PATENT DOCUMENTS

2005/0078797 A1* 4/2005 Danielsson et al. ......... 378/145
2005/0129172 A1 6/2005 Mertelmeier

FOREIGN PATENT DOCUMENTS

DE 103 53 611 A1 6/2005

* cited by examiner

*Primary Examiner*—Hoon Song
(74) *Attorney, Agent, or Firm*—Brinks, Hofer, Gilson & Lione

(57) ABSTRACT

The present embodiments relate to a mammograph system with a face shield. The mammography system includes an X-ray emitter head; an object table; and a face shield. The face shield is movably supported by the X-ray emitter head and is movable into at least first and second positions. In the first position, the face shield is retracted into the X-ray emitter head. In the second position, at least a portion of the face shield protrudes out of the X-ray emitter head.

20 Claims, 1 Drawing Sheet

MAMMOGRAPH SYSTEM WITH A FACE SHIELD

The present patent document claims the benefit of the filing date of DE 20 2005 013 910.6, filed Sep. 2, 2005.

BACKGROUND

1. Field

The present embodiments relate to a mammograph system with a face shield.

2. Related Art

Mammograph systems with a face shield have been previously used. Typically, a mammograph system includes an object table and an X-ray emitter head. A breast to be examined is positioned on the object table. The X-ray emitter head accommodates at least one X-ray source. The X-ray emitter head is typically pivotable and is generally positioned above the object table. The X-ray emitter head makes an X-ray image of the breast to be examined. The X-ray detector is located in or below the object table. A patient to be examined typically stands in front of the mammograph system.

During the operation of a mammogram, a patient approaches close to the mammograph system. The patient's breast is then fixed on the object table and compressed by a compression plate. The patient's head should not move into the beam path between the X-ray emitter head and the object table. A face shield is disposed at the height of the patient's head on the X-ray emitter head to prevent the patient's head from entering the beam path. The face shield is usually made of plastic, which provides a pleasant thermal and tactile feeling on the patient's skin. The face shield is slipped on the X-ray emitter head. Depending on the examination, the face shield can be removed or a face shield of a different length can be slipped on.

Conventionally, the face shield or multiple face shields are manipulated separately from the rest of the mammograph system. This makes storing the face shields more complicated and increases the risk that a shield will be lost. Two or more face shields are necessary to provide a variety to the face shield characteristics. There is also the danger that the face shield will suffer material fatigue and be damaged from being frequently installed and removed from the mammograph system.

SUMMARY

A mammograph system with a face shield that is adjustable and simple to manipulate is desired. The present embodiments are directed to a mammograph system with a face shield.

In one exemplary embodiment, a mammograph system includes an X-ray emitter head. A face shield is supported movably in the X-ray emitter head and is movable at least into a position of repose and into a protection position. When in the repose position, the face shield is retracted into the X-ray emitter head. When in a protection position, at least a portion of the face shield protrudes from the X-ray emitter head. When in the protection position, the face shield prevents a patient's body, more specifically, a patient's head, from unintentionally entering the region below the X-ray emitter head in the mammograph system.

The face shield, which is supported by the X-ray emitter head, makes additional storage provisions unnecessary. In the repose position, the face shield is retracted into the X-ray emitter head and is removed from the entire working area and from the surroundings of the mammograph system. Because the face shield is supported in the X-ray emitter head, it is unnecessary to install or remove the face shield, possibly resulting in no or less material fatigue or even damage. When a patient is positioned at the mammograph system, the face shield can be moved outward or retracted, something that is difficult to do in conventional systems.

In one exemplary embodiment, the face shield can be locked in a predetermined first protection position. The term locking is broadly defined as a manual lock or an automatic lock. For example, the face shield may be locked by a detent position. A first predetermined protection position may be set, and thus the face shield can be easily adjusted without close attention on the part of the equipment operator.

In another exemplary embodiment, the face shield can be locked in a second predetermined protection position. As a result, a second protection position can easily be assumed, which enhances the variability.

In an alternate embodiment, regardless of the predetermined protection position or positions, the face shield is designed to be locked in any suitable protection position.

In another exemplary embodiment, the face shield is movable into a transporting position. In the transporting position, the face shield covers the X-ray beam opening of the X-ray emitter head. The shutter element, including filters and mirrors for light visors, are located behind the X-ray beam opening, as is the X-ray source. Dirt can damage the vulnerable filter by dropping through the X-ray beam opening. The image quality of the X-ray is dependent upon the cleanliness of the filter. Accordingly, it is important that the filter be protected against dirt particles that may drop into it.

Further exemplary embodiments will become apparent from the ensuing description of the drawings.

DETAILED DESCRIPTION

Figure 1:
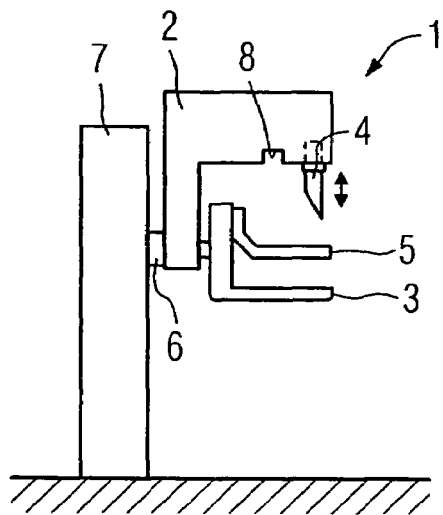
FIG. 1 shows a mammograph system with the face shield extended according to an exemplary embodiment.

According to one exemplary embodiment, a mammograph system 1 includes a floor stand 7 that supports an X-ray emitter head 2. The X-ray emitter head 2 is supported by a receptacle 6 that is rotatable about a horizontal axis. An object table 3 is supported rotatably by the X-ray emitter head 2. A patient's breast to be examined is placed on the object table. In conjunction with the object table 3, a compression plate 5 serves to fix and/or compress the breast on the object table 3.

The X-ray emitter head 2 includes an X-ray source, a shutter element, and a filter or filters (not shown). The X-ray source generates an X-ray. The X-ray, after passing through the shutter element and the filter or filters, leaves the X-ray emitter head 2 through the X-ray beam opening 8. After passing through the breast to be examined the X-ray strikes the object table 3. The compression plate 5 located between the X-ray beam opening 8 and the object table 3 is made from a radio transparent material, for example, but not limited to, a suitable plastic. An X-ray detector (not shown) is disposed inside the tabletop of the object table 3 and detects the X-rays that strike the detector. The upper side of the object table 3 is made from a radio transparent material, for example, a suitable plastic or carbon fiber. In an alternative embodiment, the X-ray detector is disposed below the object table 3, and thus the entire object table 3 is composed of a radio transparent material.

A patient (not shown) to be examined is positioned in front of the object table 3, for example, to the right of the mammography system shown in FIG. 1. A face shield 4 is supported in the X-ray emitter head 2. The face shield 4 is positioned at approximately the height of the patient's head. The face shield 4 protrudes from the X-ray emitter head 2 outside the beam path between the X-ray beam opening 8 and the object table 3, and thus the patient's head is prevented from entering the beam path.

In one exemplary embodiment, as shown in FIG. 1, the face shield 4 has an upper part located inside the emitter head (shown with dashed lines). The face shield 4 is supported movably in the X-ray emitter head 2 in the vertical direction, which is represented by a double arrow in FIG. 1. The face shield 4 is made of, but not limited to, plastic.

Figure 2:
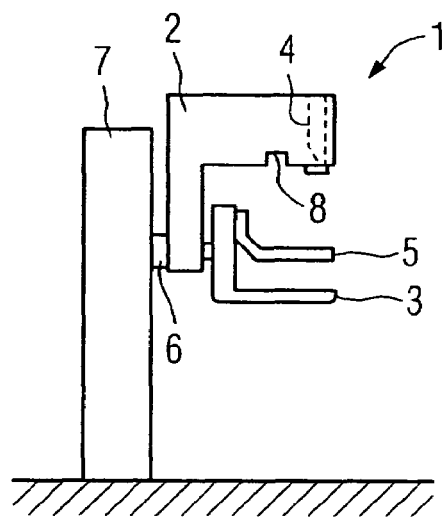
FIG. 2 shows a mammograph system with the face shield retracted according to an exemplary embodiment.

In another exemplary embodiment, as shown in FIG. 2, the mammograph system 1 includes a face shield 4 that is retracted. The face shield 4 is positioned all the way into the X-ray emitter head 2 (shown by dashed lines in the drawing). In this embodiment, the face shield 4 can be easily stored.

Figure 3:
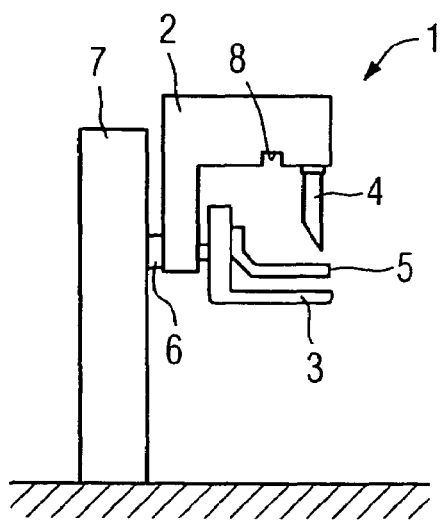
FIG. 3 shows a mammograph system with the face shield extended into a second position according to an exemplary embodiment.

In an exemplary embodiment, as shown in FIG. 3, the mammograph system 1 includes a compression plate 5 at an altered height and with a fully extended face shield 4. An altered height of the compression plate 5 may be necessary for different examinations as well as for different patients. The face shield 4 is extended to a protection position, which is adapted to the altered height of the compression plate 5. The face shield 4 and the compression plate 5 may be altered independently. For example, the face shield 4 may be extended without altering the height of the compression plate.

The face shield 4 may be locked in a desired position. For example, the face shield 4 may be locked in a first predetermined protection position, as shown in FIG. 1. The locking can be done either manually, for example, by actuating a lever, or automatically, for example, as a detent position.

As shown in FIG. 3, a second protection position of the face shield 4 is shown, which can also be manually or automatically locked at a predetermined protection position. The face shield 4 is not limited to the first and second protection positions, for example, other desired positions may be chosen. Alternatively, the face shield 4 can be variably adjustable, for example, without predefined working positions.

Figure 4:
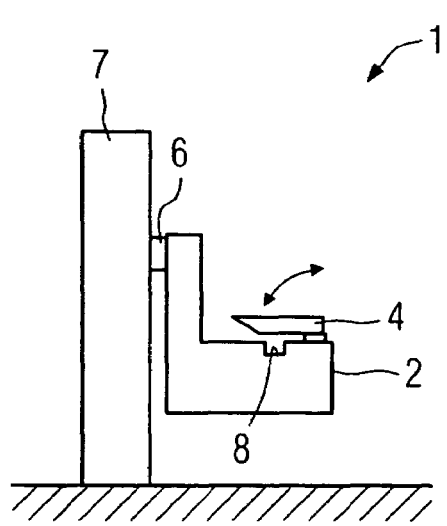
FIG. 4 shows a mammograph system with a face shield in the transporting position according to an exemplary embodiment.

In one exemplary embodiment, as shown in FIG. 4, the mammograph system 1 includes an X-ray emitter head 2 in a parked or transport position. In the parked position, the X-ray emitter head 2 is pivoted into a low position, as seen in the drawing, in which the X-ray beam opening 8 points upward. This position is used, but not limited to, during manufacture at the factory, when being transported, when being installed, or in mobile use of the mammograph system.

In another exemplary embodiment, the face shield 4 is pivoted into a transporting position, which covers the X-ray beam opening 8. The low position of the X-ray beam opening 8 makes is even more vulnerable than usual to the penetration of dust or dirt particles. The face shield 4 in a transporting position helps to prevent dust or dirt particles from damaging the X-ray beam opening 8. Alternatively, the face shield 4 can be pivoted completely flush onto the X-ray beam opening 8, which protects against soiling of the filters, shutter elements and the X-ray source in the X-ray emitter head 2. The face shield 4 with a pivoting mechanism is not the only device that may be provided for covering the X-ray beam opening 8.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

What is claimed is:

1. A mammograph system comprising an X-ray emitter head; an object table; and a face shield that is movably supported by the X-ray emitter head and is movable into at least first and second positions,
    wherein in the first position the face shield is retracted into the X-ray emitter head, and
    wherein in the second position at least a portion of the face shield protrudes out of the X-ray emitter head.

2. The mammograph system as defined by claim 1, wherein the face shield is operable to be locked in a predetermined first protection position comprising the second position.

3. The mammograph system as defined by claim 2, wherein the face shield is operable to be locked in a second predetermined protection position.

4. The mammograph system as defined by claim 1, wherein the face shield is operable to slide into the first position.

5. The mammograph system as defined by claim 1, wherein the face shield is movable into a transporting position, which covers an X-ray beam opening of the X-ray emitter head.

6. The mammograph system as defined by claim 5, wherein the face shield is operable to pivot into the transporting position.

7. An X-ray emitter head comprising:
    a face shield comprising a single plates,
    wherein the face shield being movable supported by the X-ray emitter head; and movable at least into a position of repose, in which the face shield is substantially retracted into the X-ray emitter head, and into a protection position, in which at least a portion of the length of the face shield protrudes from the X-ray emitter head,
    wherein the length that the face shield protrudes from the X-ray emitter head is independent of a height of a compression plate.

8. The X-ray emitter head as defined by claim 7, wherein the face shield is operable to be locked in a predetermined first protection position.

9. The X-ray emitter head as defined by claim 8, wherein the face shield is operable to be locked in a second predetermined protection position.

10. The X-ray emitter head as defined by claim 7, wherein the face shield is operable to slide into the protection position.

11. The X-ray emitter head as defined by claim 7, wherein the face shield is movable into a transporting position, which covers the X-ray beam opening of the X-ray emitter head.

12. The X-ray emitter head (2) as defined by claim 11, wherein the face shield is operable to pivot into the transporting position.

13. The mammograph system as defined by claim 1, wherein the face shield prevents a patient's body from unintentionally entering the region below the X-ray emitter head.

14. The mammograph system as defined by claim 1, wherein the face shield prevents a patient's head from unintentionally entering the region below the X-ray emitter head.

15. The mammograph system as defined by claim 3, wherein the face shield is operable to slide into the first position.

16. The X-ray emitter head as defined by claim 8, wherein the face shield is operable to slide into a predetermined first protection position.

17. The X-ray emitter head as defined by claim 9, wherein the face shield is operable to slide into a predetermined second protection position.

18. The mammograph system as defined by claim 2, wherein in the predetermined first protection position, a portion of the face shield extends from the X-ray emitter head.

19. The mammograph system as defined by claim 18, wherein the face shield extends further from the X-ray emitter head in the predetermined second protection position than in the first protection position.

20. The mammograph system as defined by claim 5, wherein the face shield is flush with the X-ray emitter head.

* * * * *